United States Patent
Calamel et al.

(10) Patent No.: US 11,318,023 B2
(45) Date of Patent: May 3, 2022

(54) ANKLE PROSTHESIS COMPRISING A TALAR IMPLANT, A TIBIAL IMPLANT AND AN INSERT, AND KIT INCLUDING AT LEAST ONE SUCH PROSTHESIS

(71) Applicant: BIOTECHNI, La Ciotat (FR)

(72) Inventors: Lionel Calamel, Plan de Cuques (FR); Franck Olivera, Pourrieres (FR); Joseph-Guy Asencio, Nimes (FR); Marion Di Schino, Nimes (FR); Christian Leonardi, Nimes (FR)

(73) Assignee: BIOTECHNI, La Ciotat (FR)

( * ) Notice: Subject to any disclaimer, the term of this patent is extended or adjusted under 35 U.S.C. 154(b) by 0 days.

(21) Appl. No.: 16/651,753

(22) PCT Filed: Sep. 28, 2018

(86) PCT No.: PCT/EP2018/076500
§ 371 (c)(1),
(2) Date: May 8, 2020

(87) PCT Pub. No.: WO2019/063807
PCT Pub. Date: Apr. 4, 2019

(65) Prior Publication Data
US 2020/0330238 A1 Oct. 22, 2020

(30) Foreign Application Priority Data
Sep. 28, 2017 (FR) ........................ 1758993

(51) Int. Cl.
*A61F 2/42* (2006.01)
*A61F 2/30* (2006.01)
*A61B 17/17* (2006.01)

(52) U.S. Cl.
CPC ........ *A61F 2/4202* (2013.01); *A61B 17/1775* (2016.11); *A61F 2002/30028* (2013.01);
(Continued)

(58) Field of Classification Search
CPC ............ A61F 2002/4633; A61F 2/4202; A61F 2002/4207; A61F 2/6607;
(Continued)

(56) References Cited

U.S. PATENT DOCUMENTS 6,409,767 B1 * 6/2002 Perice ................... A61F 2/4202
                                                                 623/21.18
8,114,091 B2 * 2/2012 Ratron .................. A61F 2/4202
                                                                 606/99
(Continued)

FOREIGN PATENT DOCUMENTS

EP     1 915 975 A1    4/2008
EP     2 363 087 A1    9/2011
(Continued)

OTHER PUBLICATIONS

Rapport De Recherche Internationale issued in corresponding International Patent Application No. PCT/EP2018/076500 dated Jan. 4, 2019, in French.
(Continued)

*Primary Examiner* — Ann Schillinger (57) ABSTRACT

An ankle prosthesis comprising a tibial implant, a talar implant and an insert to articulate the implants. The top face of the tibial implant having an anchoring fin, and the bottom face is articulated with the top surface of the insert. The bottom face of the talar implant includes an anchor to the talar bone, and the top face is articulated with the bottom surface of the insert. The articulation surface being saddle-shaped and including a longitudinal central groove allowing the insert to move longitudinally and rotate transversely. The top face of the tibial implant includes, on its anterior edge, a shield covering the bottom anterior portion of the tibia, and the tibial face is inclined and forms an angle with the horizontal of between 15° and 45°. Passages are provided in
(Continued)

the shield for bone screws passing through in an ascending manner and open on the inclined tibial face.

16 Claims, 5 Drawing Sheets

(52) U.S. Cl.
CPC .............. *A61F 2002/30156* (2013.01); *A61F 2002/30578* (2013.01); *A61F 2002/30884* (2013.01); *A61F 2002/4205* (2013.01); *A61F 2002/4207* (2013.01)

(58) Field of Classification Search
CPC ...... A61F 2002/0829; A61F 2002/0882; A61F 2002/30205; A61F 2002/30616; A61F 2002/30878; A61F 2002/4205; A61F 2002/6642; A61F 2/66; A61F 2002/30028; A61F 2002/30156; A61F 2002/30578; A61F 2002/30884; A61F 2002/30253; A61F 2002/30576; A61F 2002/30649; A61F 2002/30785; A61B 17/1775; A61B 17/1682; A61B 17/7291; A61B 17/846; A61B 17/86
See application file for complete search history.

(56) References Cited

U.S. PATENT DOCUMENTS

| | | | |
|---|---|---|---|
| 8,303,667 B2* | 11/2012 | Younger | A61F 2/64 623/21.18 |
| 2006/0142870 A1* | 6/2006 | Robinson | A61B 17/142 623/21.18 |
| 2006/0247788 A1* | 11/2006 | Ross | A61F 2/4202 623/21.18 |
| 2007/0225813 A1* | 9/2007 | Haines | A61F 2/4425 623/17.16 |
| 2008/0103603 A1* | 5/2008 | Hintermann | A61F 2/4606 623/20.32 |
| 2008/0109081 A1* | 5/2008 | Bao | A61F 2/38 623/17.15 |
| 2011/0035019 A1* | 2/2011 | Goswami | A61F 2/4202 623/21.18 |
| 2011/0166608 A1* | 7/2011 | Duggal | A61B 17/7233 606/320 |
| 2013/0041473 A1* | 2/2013 | Rouyer | A61F 2/4202 623/21.18 |
| 2015/0320567 A1* | 11/2015 | Terrill | A61F 2/4202 623/21.18 |
| 2019/0070012 A1* | 3/2019 | Leemrijse | A61F 2/30749 |

FOREIGN PATENT DOCUMENTS

| | | | | |
|---|---|---|---|---|
| FR | 2 759 900 A1 | | 8/1998 | |
| FR | 2759900 A1 | * | 8/1998 | ........... A61F 2/4606 |
| WO | 00/69373 A1 | | 11/2000 | |
| WO | 01/89427 A1 | | 11/2001 | |

OTHER PUBLICATIONS

Rapport De Recherche Pre Liminaire issued in corresponding French Patent Application No. FR1758993 fated Jun. 14, 2018, in French.

* cited by examiner

ANKLE PROSTHESIS COMPRISING A TALAR IMPLANT, A TIBIAL IMPLANT AND AN INSERT, AND KIT INCLUDING AT LEAST ONE SUCH PROSTHESIS

CROSS REFERENCE TO RELATED APPLICATIONS

This is a U.S. National Phase Application under 35 U.S.C. § 371 of International Patent Application No. PCT/EP2018/076500, filed Sep. 28, 2018, which claims priority of French Patent Application No. FR 17 58993, filed Sep. 28, 2017. The entire contents of which are hereby incorporated by reference.

BACKGROUND

The present invention relates to an ankle prosthesis of the type comprising a talar implant, a tibial implant and an insert on which these two implants are articulated.

Ankle prostheses are known including the three aforementioned elements. One is described in document WO-A-00/69373.

SUMMARY

It includes a talar implant with a curved bottom surface and bearing, on its bottom face, two spikes oriented obliquely toward the rear of the prosthesis. This bottom surface constitutes the interface between the talar implant and the bone of the heel. The spikes are used to anchor the talar implant on the bone of the heel. The top surface of the talar implant is in the shape of a "saddle", that is to say, it is provided with a longitudinal groove (in other words, extending between the front and the back of the body of the patient and the prosthesis, and not between the right and the left of the body of the patient and the prosthesis, like a transverse groove would do). The transverse section of the groove has a curve radius and the groove separates the top surface of the talar implant into two portions connected to one another by inflection lines along which the curvature direction reverses. Each of these portions is shaped as a sphere portion.

It also includes a tibial implant, intended to be fastened to the bottom end of the tibia adequately molded by the surgeon beforehand. Its top surface has a generally substantially planar shape and includes bone anchoring means made up of two cylinders that are inserted in the housings arranged in the tibia to that end. Its bottom surface is substantially spherical.

It lastly includes an insert placed between the two preceding implants, and the bottom and top faces of which have shapes corresponding to those of the respective implants with which they are in contact. Thus, on the one hand, the connection between the insert and the tibial implant works like a ball joint, and on the other hand, there is a possibility of longitudinal sliding of the insert over the top surface of the talar implant. In this way, the natural relative movements between the tibia and the talar bone are optimally reproduced owing to the prosthesis.

Another example of an ankle prosthesis in three such parts appears in document EP-A-1,915,975. The talar implant has a curved bottom surface that includes two anchoring spikes. This anchoring on the talar bone is completed by an anterior fastening tab allowing screws to pass and by lateral flanges that frame the talar bone. The fastening of the tibial implant on the tibia is provided by points arranged on the planar top surface of the tibial implant and by a vertical transverse stop, that is to say, substantially perpendicular to the planar top surface of the tibial implant, which is positioned on the anterior edge of the tibial implant. It forms a tibial shield, which, in addition to its function of keeping the tibial implant in place, prevents an inappropriate development of bone cells that may bother the working of the joint. The insert has a bottom face whose geometry corresponds to that of the top face of the talar implant and a top face whose geometry corresponds to that of the bottom surface of the tibial implant. One particularity of this prosthesis is that it includes an example of configurable coupling means designed to permit the adjustment of the position of the insert relative to the tibial implant. This adjustment is obtained inter alia by coupling means such as compression screws that pass through the shield of the tibial implant and are oriented toward the insert.

This latter configuration of the tibial implant, with its anterior tibial shield substantially vertical, is not optimal, however, since upon use, one realizes that when the tibia is osteoporotic, fastening of the tibial implant by impaction, like in the examples that have been described, is not sufficient to obtain good stability of the tibial implant, in particular to avoid rotations about the medio-lateral axis thereof, which would cause it to tilt forward or backward. The addition of screws, passing through the vertical tibial shield in order to be anchored on this insufficiently healthy bone, would not constitute a satisfactory solution to this situation.

The aim of the invention is to propose an improvement to the known ankle prostheses made from three elements that can be used on patients suffering from osteoporosis, in particular in the tibia, with excellent stability.

To that end, the invention relates to an ankle prosthesis including a tibial implant, a talar implant and an insert with which said implants are articulated, according to which:

the top face of the tibial implant comprises at least one anchoring fin of the tibial implant in the tibia of the patient, and the bottom face of the tibial implant is a surface articulated with the top surface of the insert;

the bottom face of the talar implant includes means for anchoring to the talar bone of the patient, and the top face of the talar implant is a surface articulated with the bottom surface of the insert, said articulation surface being saddle-shaped and including a longitudinal central groove in which the insert can move longitudinally and rotate transversely;

characterized in that the top face of the tibial implant includes, on its anterior edge, a shield intended to cover the bottom anterior portion of the tibia of the patient, and the tibial face of which is inclined and forms an angle ($\alpha$) with the horizontal of between 15° and 45°, and in that passages are provided in this shield for bone screws that pass through the shield in an ascending manner and open on the inclined tibial face thereof.

The bottom face of the tibial implant can be convex and in a sphere portion and have a curve radius, and the top face of the insert is then concave in a sphere portion and has a curve radius equal to that of the bottom face of the tibial implant.

The bottom face of the tibial implant can be convex and have a first curve radius in the anterior-posterior plane of the prosthesis, and a second curve radius in the medial-lateral plane of the prosthesis, and the top surface of the insert is then concave and has the same curve radii as the bottom face of the tibial implant, the difference between said first and second curve radii being between 1 and 5% of said second curve radii.

The anchoring means of the talar implant can include at least one transverse fin inclined relative to the bottom surface of the talar implant by an angle (β) oriented toward the rear of the prosthesis and the value of which is between 20 and 70°, preferably between 30 and 50°.

The talar implant can then include at least two transverse fins positioned side by side.

The width of the transverse fin or the sum of the widths of the transverse fins placed side by side can represent between 40 and 80% of the width of the talar implant.

The at least one fin for anchoring the tibial implant in the tibia of the patient can be in the general shape of a right-angled triangle, the hypotenuse of which rests on the top face of the tibial implant and the small side of which is oriented toward the front of the tibial implant.

The length of the hypotenuse of the tibial fin can represent between 50% and 80% of the total length of the top face of the tibial implant.

The upper corner of the tibial fin can be between 80° and 120°.

The at least one anchoring fin of the tibial implant and the anchoring means of the talar implant preferably have not undergone any surface treatment intended to promote bone growth, whereas other portions of said implants intended to be in contact with the tibia or the talar bone have preferably undergone such a surface treatment.

The invention also relates to a kit comprising a plurality of ankle prostheses of the preceding type, characterized in that said prostheses have different sizes, but all have identical curve radii on the bottom faces of their tibial implants and on the top faces of their inserts.

The invention also relates to a kit including at least one ankle prosthesis of the preceding type, characterized in that it also includes a cutting guide for preparing the tibia to receive the shield of a tibial implant of the preceding type.

It may also include a cutting guide for preparing the tibia to receive the shield of a tibial implant of the preceding type.

As one will have understood, the invention is based on the presence of the tibial implant of an anterior tibial shield that has two essential features distinguishing it from the vertical anterior tibial shield known in EP-A-1,915,975.

The first of these features is that the posterior face of the shield (that which is in contact with the tibia) does not form a right angle with the horizontal top surface of the tibial implant, but forms an angle on the order of 30°, more specifically between 15° and 45°, therewith. Before the installation of the prosthesis, the end of the tibia of the patient is shaped by the surgeon to be able to be in contact with the shield over the entire surface thereof, including the posterior surface inclined at 15-45°. This configuration guarantees that the implant will not tilt forward or backward, as described in the case of EP-A-1,915,975.

To that end, and this is the second of the main distinctive features, the fastening of the tibial implant is completed by bone screws that pass through the inclined shield while being oriented obliquely upward, and are anchored in the tibia.

The use of such screws, anchored horizontally in the tibia, is also considered in the case of the implants with vertical shield of the prior art, but if they are not placed correctly, and/or are placed on a bone of quality deteriorated by osteoporosis, they do not prevent tilting of the implant. The invention makes it possible to secure the placement and holding in place of the tibial implant, even on an osteoporotic bone, and therefore to make the working of the ankle prosthesis reliable over time.

The fact that the shield does not cover the substantially vertical anterior face of the tibia, but only a portion of its bottom end made oblique, causes it to bear part of the substantially vertical force that it exerts on this bottom end, and this also helps keep it in place during the use of the prosthesis.

The shaping of the bottom end of the tibia, which must be done before the placement of the tibial implant, includes, in addition to the horizontal cutting that is also necessary for conventional tibial implants, an interior cutting of the end of the tibia in order to form a plane whose incline corresponds to that of the shield. However, this is not a real drawback. The surgeon can, to that end, use an appropriate cutting guide, and perform both cuts in the same motion. The placement time of the prosthesis and the difficulty of this placement are therefore not substantially affected as a result.

BRIEF DESCRIPTION OF DRAWINGS

The invention will be better understood upon reading the following description, given in reference to the following appended figures.

It must be understood that the exemplary embodiment of the invention that will be described is merely one non-limiting example, which, in addition to the anterior shield inclined by about 30° relative to the horizontal, which is the heart of the invention, has a certain number of other advantageous features that may be combined with one another in various ways, as chosen by the manufacturer of the prosthesis and the wishes of its clients, as will be discussed hereinafter.

DETAILED DESCRIPTION OF DRAWINGS

Figure 1:
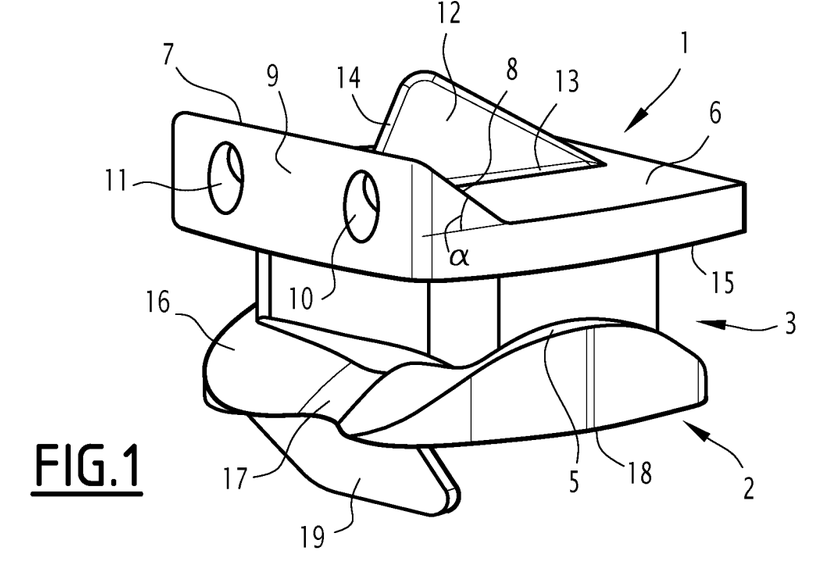
FIG. 1, which shows an exemplary ankle prosthesis according to the invention, in perspective view.
Figure 2:
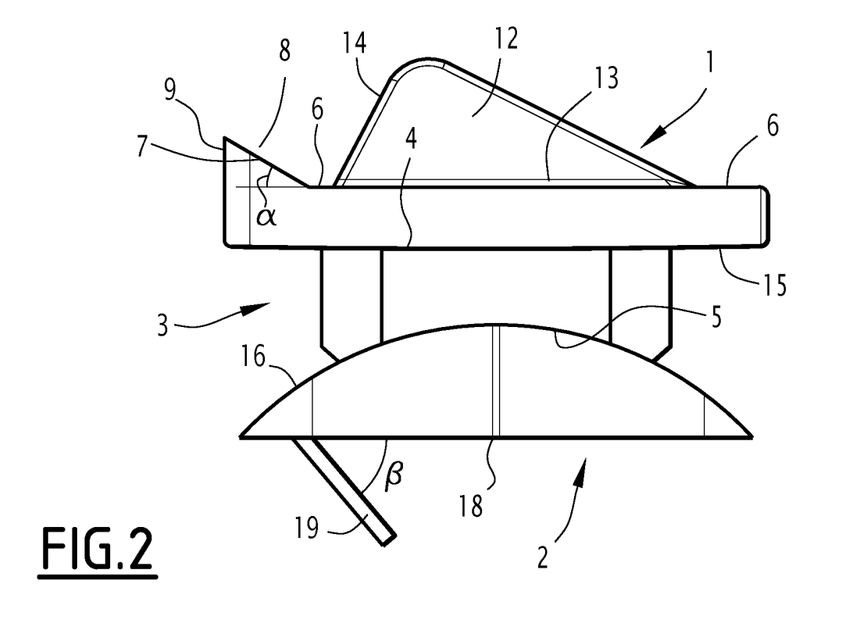
FIG. 2, which shows this same example in profile view.

FIGS. 1 and 2 show the three elements of an exemplary prosthesis according to the invention, assembled to one another in their usual relative positions that they are meant to occupy when the prosthesis is installed and the ankle of the patient is at rest.

Figure 3:
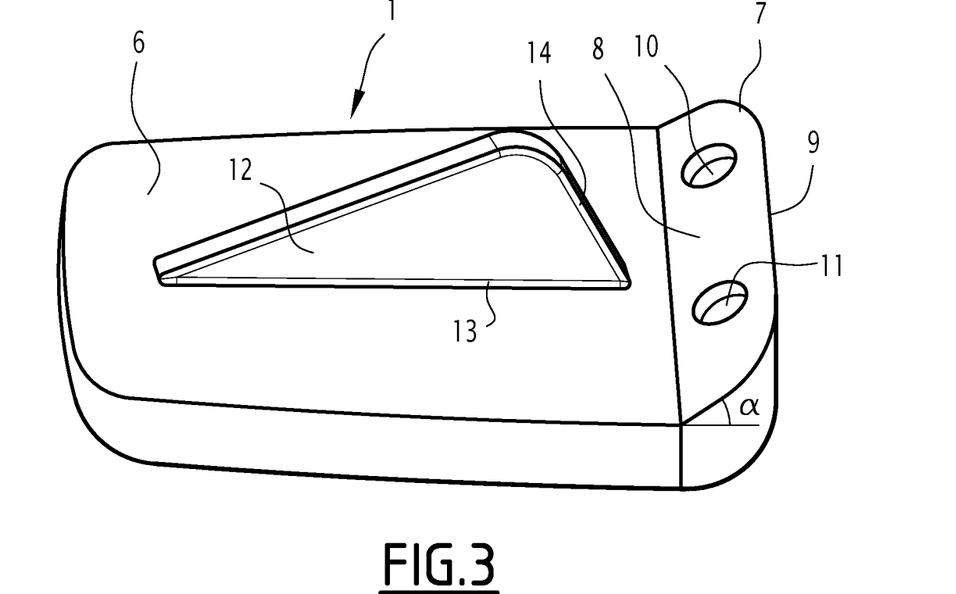
FIG. 3, which shows the tibial implant of FIGS. 1 and 2 in top perspective view.
Figure 4:
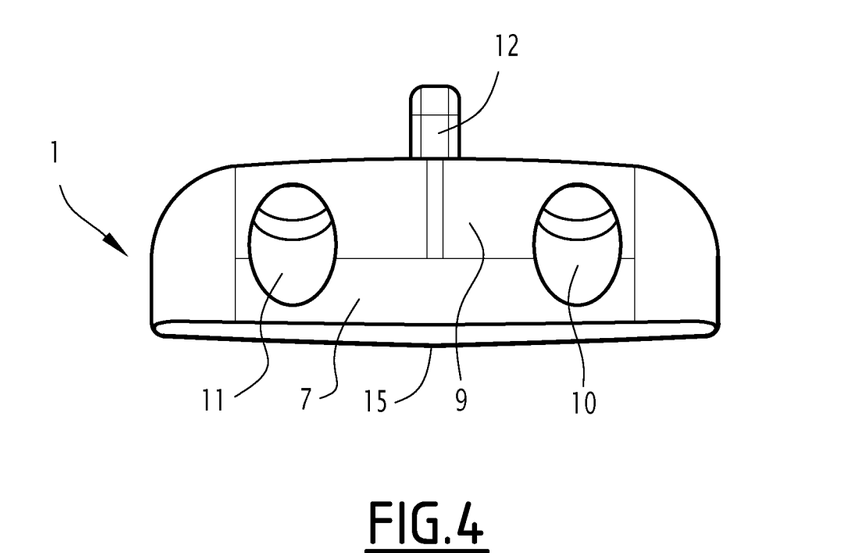
FIG. 4, which shows this same tibial implant in front view.
Figure 5:
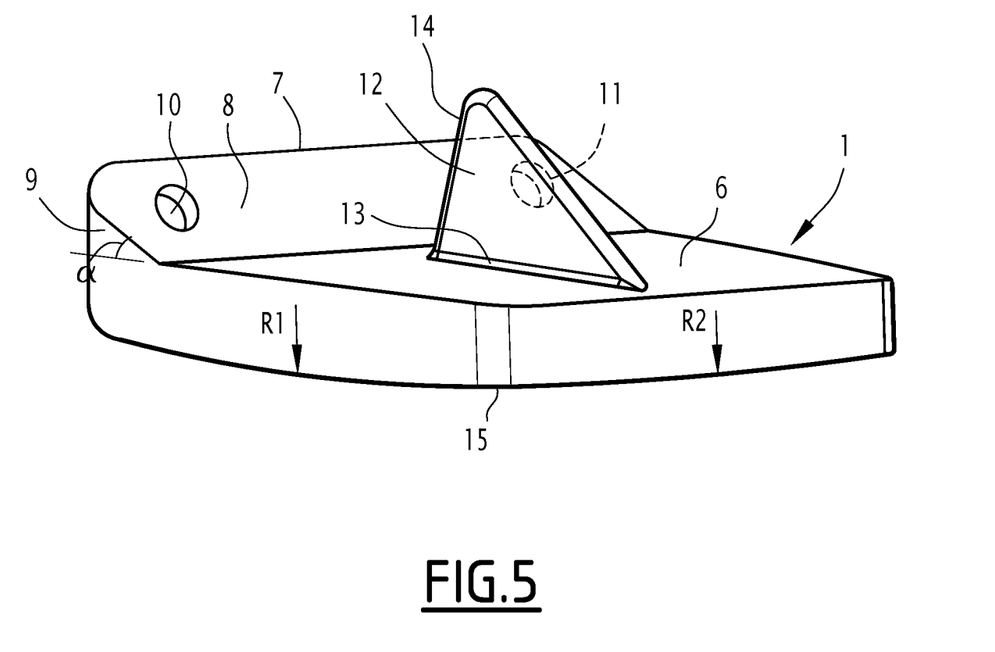
FIG. 5, which shows a variant of this same tibial implant, seen in posterior perspective view.

The first element of the prosthesis is a tibial implant 1 anchored on the bottom end of the tibia of the patient appropriately shaped beforehand, and shown alone in FIGS. 3, 4 and 5.

The second element of the prosthesis is a talar implant 2 anchored on the top face of the talar bone molded appropriately beforehand.

The third element of the prosthesis is an insert 3, having a top surface 4 on which the tibial implant 1 is articulated, and a bottom surface 5 on which the talar implant 2 is articulated.

We will first describe the tibial implant 1.

It has outer dimensions that make it appropriate for fastening to the bottom end of the tibia of the patient, shaped beforehand to that end, as is conventional.

Its top face 6 is generally planar and rectangular, but it has two specific elements.

According to the invention, on its anterior edge, which corresponds to the anterior edge of the tibia of the patient, it has a shield 7 that is intended to cover the anterior bottom portion of the tibia of the patient. Unlike what happens in document EP-A-1,915,975, already cited, this shield is not vertical, but has a tibial contact face 8 with the tibia, which forms an angle α with the horizontal (in other words, the extension of the top face 6 of the implant), this angle α being open toward the front of the prosthesis and being between 15 and 45°, typically equal to 30°. The anterior face 9 of the shield 7, that is to say, the face opposite this inclined tibial face 8, is vertical in the illustrated example, as is preferable, without, however, being mandatory. Such a vertical anterior face 9 increases the thickness of the shield relative to an oblique anterior face 9, therefore increases its stiffness, and is also favorable for the effectiveness of the anchoring screws.

Two passages 10, 11 are made through this anterior face 9 for the passage of bone screws (not shown). These passages 10, 11 pass through the shield 7 in an ascending direction, preferably forming an angle of 60° to 80° with the horizontal.

The bone screws emerge on the inclined tibial face 8 of the shield 7, and are housed in the tibia of the patient while providing good securing of the tibial implant 1 to the tibia. It is not necessary for the bone screws to emerge perpendicular to the posterior face 8 of the shield 7, therefore said angle that the passages 10, 11 form with the horizontal is not dependent on the value of said angle α.

The angulation α at 15-45° of the shield 7, according to the invention, ensures that the tibial implant 1 will not experience tilting from front to back or vice versa during its use, and that it will remain perfectly horizontal, as long as the prior cutting of the tibia has been done correctly. This cutting is subject to the same constraints as for the implant of EP-A-1,915,975, to which is added the shaping of the surface of the tibia on which the inclined tibial face 8 of the shield 7 will be pressed. However, this shaping is done by an appropriate cutting guide, in the same motion as the shaping of the bottom face of the tibia on which the top face 6 of the tibial implant 1 will rest. One such exemplary cutting guide will be described later.

This securing of the tibial implant 1 to the tibia is also provided by a fin 12 positioned on the top face 6 of the implant 1 and which extends preferably over the majority of the longitudinal axis of said face 6 (that is to say, of the axis that goes from the posterior part to the anterior part of the implant). This fin is generally in the shape of a right-angled triangle and must be inserted into the tibia of the patient.

The use of fins approximately in the shape of a right-angled triangle on a tibial implant is already known in the prior art. These known fins, however, have a shape that is substantially different from that which the invention preferably includes. Typically, the fins approximately in the shape of a right-angled triangle have the small side of the triangle resting on the top surface of the tibial implant, and their hypotenuse (which can in fact be slightly curved) facing toward the front of the tibia. They therefore have a relatively significant height and are inserted into the medullary cavity of the tibia, arranged beforehand to that end.

The fin 12 as shown, according to one preferred variant of the invention, on the contrary has its hypotenuse 13 resting on the top face 6 of the tibial implant 1. The small side 14 of the fin is oriented toward the front of the tibial implant 1, therefore toward the shield 7.

Relative to the conventional configuration of the fins in a very high right-angled triangle, the configuration according to one preferred variant of the invention that has just been described has various advantages.

Due to its smaller dimensions, this fin shape 12 requires less healthy bone to be removed than the conventional fins, which are narrower, but have a great height. The tibia is therefore less embrittled, which is especially important if the patient is suffering from osteoporosis. The conventional fins are more likely to result in the unwanted formation of bone geodes. Additionally, having the hypotenuse 13 placed on the top surface 6 of the tibial implant 1, with the small side 14 of the fin oriented toward the front of the tibia, makes it possible to have both a relatively small height of the fin 12 and a large contact surface of the fin 12 with the top surface 6 of the tibial implant 1, resulting in a good distribution of the forces exerted on the tibial implant 1 during walking, which is favorable to good holding of the tibial implant 1 over time.

It is considered that preferably, the length of the hypotenuse 13 of the fin 12 represents 50% to 80%, typically 70%, of the total length of the top face 6 of the tibial implant 1, said total length therefore including the portion on which the shield 8 is present.

Preferably, the height of the fin 12 represents 60% to 80% of the total height of the tibial implant 1, typically ⅔ of this height.

As stated, the fin 12 is generally in the shape of a right-angled triangle, but the top corner, as shown, can be rounded, is not necessarily strictly equal to 90°, and can be located in a range from 80° to 120°.

Preferably, the fin 12 has a width of between 2 and 3 mm, for example about 2.5 mm. There is a compromise to be found between the small thickness that does not require removing much healthy bone and a large thickness that improves the solidity of the anchoring, if the bone can accept it. In the illustrated variant, a space is kept between the anterior end of the base of the fin 12 and the base of the shield 8. However, this is only one embodiment variant, and it would still be compliant with the invention to have the base of the fin 12 abut against the base of the shield 8.

It is possible to consider the presence of several parallel fins 12 instead of just one, like in the illustrated example.

Regarding the bottom surface 15 of the tibial implant 1, it must be capable of procuring a possibility of articulation with the corresponding top surface 4 of the insert 3, so as to contribute to restoring its natural movements to the ankle of the patient. It is thus possible to impart, to this bottom surface 15, a convex shape substantially in a sphere portion, and having a curve radius R substantially identical to that which the top surface 4 of the insert 3 has, the latter being the "negative" of the bottom surface 15 of the tibial implant 1, and therefore being concave in a sphere portion, so as to articulate the tibial implant 1 and the insert 3 one on the other like a ball joint. Typically, this radius R is of the order of 300 to 310 mm.

Another possibility would be for this bottom surface 15 of the tibial implant 1 to be convex and not to have a single curve radius, but, as shown in FIG. 5, which shows this configuration, two different curve radii: one curve radius R1 in the anterior-posterior plane and another curve radius R2 in the medio-lateral plane. R2 is greater than R1 in the illustrated example, but the reverse would also be conceivable. The differences between these two radii R1 and R2 must, however, remain small in order to the ensure proper working of the articulation, of the order of 1 to 5%, this percentage being calculated on the basis of R2.

In this variant, this configuration with two curve radii would preferably be found substantially identically on the top surface 4 of the insert 3.

Typically, R1 can be 305 mm and R2 can be 310 mm.

In general, it is preferable to have a congruence of the surfaces of the tibial implant 1 and the insert 3 that are in contact with one another (in other words, substantially identical curve radii), so as to have a good distribution of the forces over the entirety of these surfaces, in particular when the articulation is in its nominal position where the contact is maximal between the tibial implant 1 and the insert 3.

It is common practice to cover the various elements of an ankle prosthesis with hydroxyapatite, or another substance promoting bone growth, in the areas where the prostheses are in contact with the bone of the patient. Another type of surface treatment, in particular a shot peening, in addition to or in place of this coating, can also contribute to this function. However, it is often observed that bone geodes can form in the coated areas when they have somewhat complex shapes. The inventors therefore deem it preferable not to arrange such a coating on the fin 12, and in general, not to treat its surface with physical or chemical means. The chemical and/or physical treatment of the surface can be limited to all or part of the top surface 6 of the tibial implant 1 and also to that of the shield 8, or in general to any part of the tibial implant 1 intended to come into contact with the tibia of the patient, other than the fin 12.

We will now describe the talar implant 2 in more detail.

It can have a general configuration according to that of the known talar implants, for example in the documents cited in the introduction. However, according to a preferred variant of the invention, it can have the configuration shown in the figures. The latter, as is the case for the prosthesis of WO-A-00/69373, has a saddle-shaped top surface 16, with a central longitudinal groove 17 in which the insert 3 can move longitudinally and rotate laterally. In this way, the articulation surfaces between the talar implant 2 and the insert 3 have shapes that match one another, and the talar implant 2 and the insert 3 can slide over one another freely in the sagittal plane, but not in the frontal plane except in rotation, which results in keeping the prosthesis in place and preventing the dislocation in case of lateral hyperlaxity of the patient's ankle. The transverse section of the groove 17 has a curve radius and the groove 17 separates the top surface 16 of the talar implant 2 into two portions connected to one another by inflection lines along which the curvature direction reverses. Each of these portions has a shape in a sphere portion.

However, this preferred configuration of the talar implant 2 has two remarkable particularities.

First, its bottom surface 18 is not curved, but planar. This simplifies the shaping of the talar bone, relative to the conventional case where this bottom surface is curved and approximately reproduces the nominal shape of the talar bone. Even in talar implants with a curved bottom surface, a shaping of the surface of the talar bone to adapt it to the implant is in any case necessary, such that the installation of the talar implant according to this preferred variant of the invention does not require an additional step relative to the most common practice. Likewise, the planar bottom surface 18 of this variant of the invention simplifies this shaping of the talar bone.

Next, the anchoring of the talar implant 2 in the talar bone is no longer ensured by substantially cylindrical spikes, but by a planar transverse talar fin 19 that is inclined relative to the bottom surface 18 of the talar implant 2 by an angle $\beta$ oriented toward the rear of the prosthesis and the value of which is between 20 and 70°, for example 45° as shown, preferably between 30° and 50° to facilitate the insertion of the fin 19 into the talar bone. The vertical size of the fin 19 is typically from 4 to 10 mm, depending on the overall size of the prosthesis, which of course depends on the measurements of the patient. The width of the talar fin 19 typically corresponds to 40 to 80% of the total width of the talar implant. The thickness of the talar fin 19 is typically of the order of 2.5 mm.

In a variant, it would be possible to have at least two such fins 19 positioned side by side and/or behind one another, even though multiplying the anchoring elements tends to increase the risks of forming bone geodes. In the case of multiple fins positioned side by side, it is the sum of their widths that should typically represent between 40 and 80% of the total width of the talar implant.

The presence of at least one transverse fin 19 as just described makes it possible to reconcile:

very good anchoring of the talar implant 2 on the talar bone; and strict flatness of the bottom surface 18 of the talar implant, which procures a lesser contact with the talar bone than in the known cases where this surface approximately follows the natural curvature of the talar bone.

The inventors recommend not treating the surface of the talar transverse fin 19 by depositing hydroxyapatite (or the like) and/or shot peening, for the same reasons as those cited with respect to the longitudinal tibial fin 12. If this treatment is done, it is therefore preferably limited to all or part of the planar bottom surface 18 of the talar implant 2, or in general, any part of the talar implant 2 intended to come into contact with the talar bone, other than the transverse fin 19.

We will now describe the insert 3.

It has, on its top face 4 and its bottom face 5, the shape and size characteristics that result from the respective shaping operations of the bottom face 15 of the tibial implant 1 and the top face 16 of the talar implant 2 as just described. Thus, the top face 4 is hollowed out with one or several curve radii substantially corresponding to that or those of the bottom face 15 of the tibial implant, and the bottom face 5 has a saddle shape that is substantially the "negative" of the saddle shape of the top surface 16 of the talar implant 2. One is therefore substantially, from this perspective, in the presence of the configuration shown in document WO-A-00/69373, already cited.

As a non-limiting example, the main dimensions of an ankle prosthesis according to the invention, in its illustrated preferred variant, would be as follows.

The tibial implant 1 has a substantially rectangular shape, or a slightly trapezoidal shape for which the large side is the anterior edge of the implant. Its length is 40.5 mm and its maximum width is 32 mm. Its total height, fin 12 included, is 15 mm. Its thickness, excluding the fin 12 and the shield 7, is about 5 mm (it varies due to the presence of the curve radii R1 and R2 and its bottom face 15). The height of the shield 7 is 10.1 mm and its length is 10 mm. The angle $\alpha$ is 30°. The radii R1 and R2 of the bottom face 15 are respectively 310 and 315 mm. The fin 12 has an apical angle of 90° and a hypotenuse with a length of 27 mm.

The talar implant 2 has a rectangular or trapezoidal general shape, although, as shown in FIG. 1, its anterior and posterior edges can each have an indentation at the outlet of the groove 17. Its length is 38 mm and its maximum width is 29.5 mm. Its maximum height is 17 mm, fin 19 included, and 9 mm excluding fin, and the curve radius of its top face 16 is 26.3 mm. Its minimum height excluding fin 17 (measured at the bottom of the groove 17) is 5.4 mm. The curve radii of the top face 16 are 29.4 mm at the groove 17 and 19.5 mm on either side of the groove 17. The fin 19 forms an angle β of 45° with the bottom face 18 of the talar implant 2; it is placed at 6 mm from the anterior edge of the talar implant 2 and extends over a height of 7.7 mm.

The insert 3 has a generally rectangular or trapezoidal shape. Its length is 26 mm and its maximum width is 28 mm. If its shape is trapezoidal, its minimum width is 24 mm. Its total maximum thickness is 10.6 mm, and its thickness, if the part intended to match the top surface 16 of the talar implant and to penetrate the groove 17 is not taken into account, varies between 5.3 mm (in the central part of the insert 3) and 8.1 mm (at the anterior and posterior edges of the insert 3). The top face 4 of the insert 3 has curves that reproduce, "in negative", those of the bottom face 15 of the tibial implant 1 that have been given.

Of course, the dimensions of the prosthesis according to the invention must be adapted to the precise morphology of the patient, and can be chosen, in particular, from the preceding example by modifying said dimensions homothetically.

One particularly advantageous way of implementing the invention consists of proposing it in the form of a kit comprising a series of prostheses, the general dimensions of which are different and able to suit patients of various morphologies. However, it is advantageous for all of the prostheses of the kit to have, on the bottom faces 15 of their tibial implants 1 and on the top faces 4 of their inserts 3, the same curve radius R (or the same curve radii R1 and R2 for the case of FIG. 5). In this way, the surgeon can choose, among the elements of the various prostheses of the kit, those that seem to him to be best suited to the exact morphology of the patient after the cuts in the tibia and the talar bone, while being assured that the two elements taken in two different prostheses will nevertheless be compatible.

The kit may also include one or several cutting guides and tools specially designed to configure the bottom end of the tibia so as to allow the placement there of the tibial implant 1 according to the invention with its shield 7. It may also include one or several other cutting guides and tools designed to configure the top surface of the talar bone, so as to allow the placement there of the talar implant 2 with the planar bottom surface 18 and inclined fin 19 included in the kit.

The cutting of the bottom end of the tibia of the patient can be done as follows.

First, a planar surface substantially perpendicular to the longitudinal axis of the tibia is cut at said bottom end. This can be done using a cutting guide and a cutting blade that are conventionally known to that end in order to place conventional tibial implants, devoid of inclined shield, for example like that disclosed in EP-A-1,915,975, already cited, which includes a vertical transverse stop bearing on the anterior face of the tibia.

Secondly, a cut is made in the bottom anterior part of the tibia so as to arrange there:

An inclined surface on which the inclined posterior face 8 of the shield 7 bears during the placement of the tibial implant 1 according to the invention;

And, if said tibial implant 1 includes, as is preferred, one or several fins 12, one or several slits in which said fin(s) 12 will be inserted during this placement.

To that end, it is possible to use, non-limitingly, the cutting guide as shown in FIGS. 6 to 9.

Figure 6:
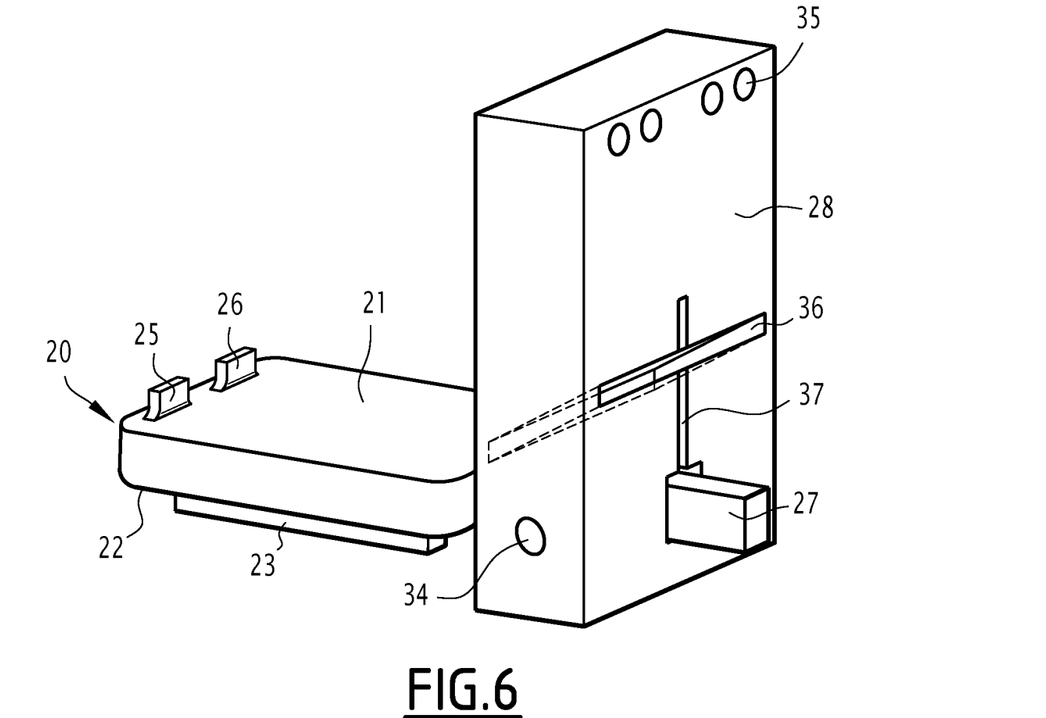
FIG. 6, which shows, inside perspective view, a cutting guide for molding the tibia for the placement of a tibial implant of the ankle prosthesis according to the invention.
Figure 7:
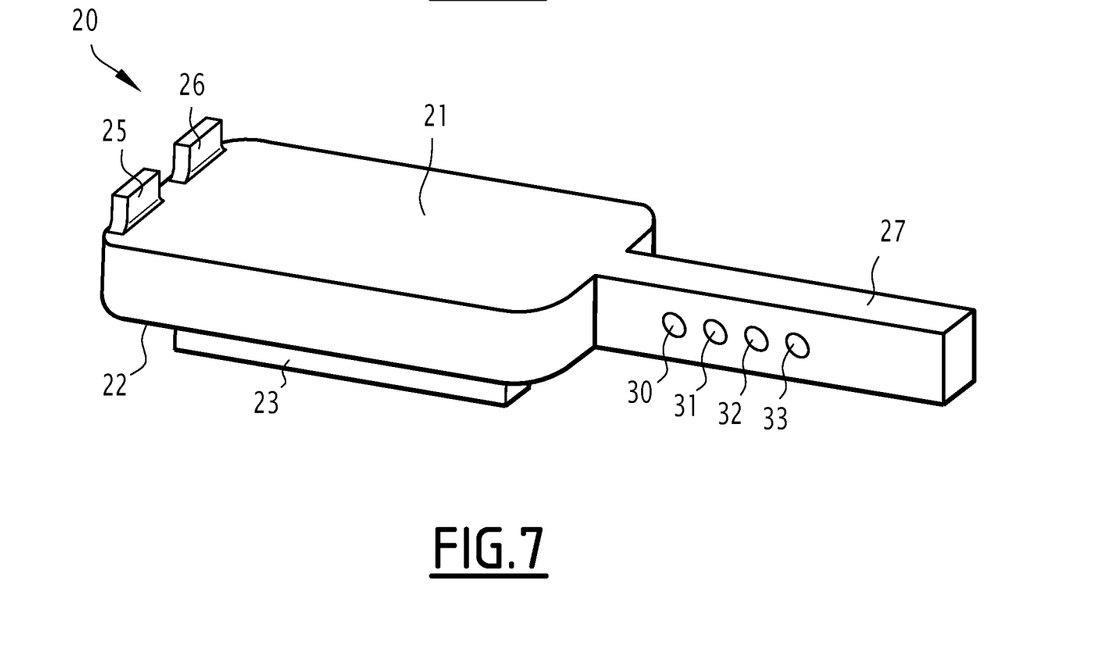
FIG. 7, which shows a top perspective view of the tray of this cutting guide.
Figure 8:
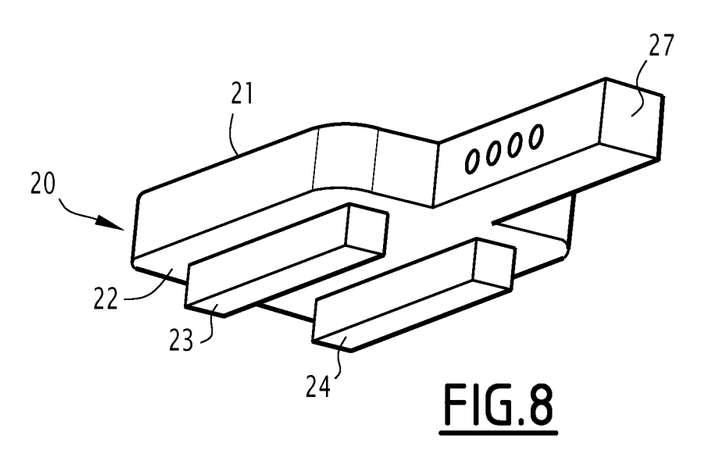
FIG. 8, which shows a bottom perspective view of this same tray.

It includes a tray 20, the top surface 21 of which is designed to bear on the planar surface substantially perpendicular to the longitudinal axis of the tibia, which has been cut during the first cutting step, and the bottom surface 22 of which includes, in the illustrated example, two rails 23, 24 that allow the tray to slide and to bear on a slotted spacer positioned on the talar bone, and which serves to impose the ligament tension that will be desired after the placement of the prosthesis, depending on its thickness combined with that of the tray 20. To that end, an operating technique called "AES" is applied that is very comparable to that described in document EP-B-1,301,148, which relates to an ankle prosthesis in three parts, the tibial implant of which, on the one hand, is devoid of the shield according the present invention, and on the other hand, includes a fin in the shape of a right-angled triangle with a significant height, the hypotenuse of which faces toward the front of the tibia, unlike a preferred variant of the present invention.

The posterior edge of the top face 21 of the tray 20 includes assistance means for the positioning and maintenance of the tray 20, which, in the illustrated example, are made up of two stops 25, 26 that are made to bear against the rear external cortex of the tibia. On the anterior edge of the tray 20 is a longitudinal appendage 27 of substantially square section in the illustrated example.

Figure 9:
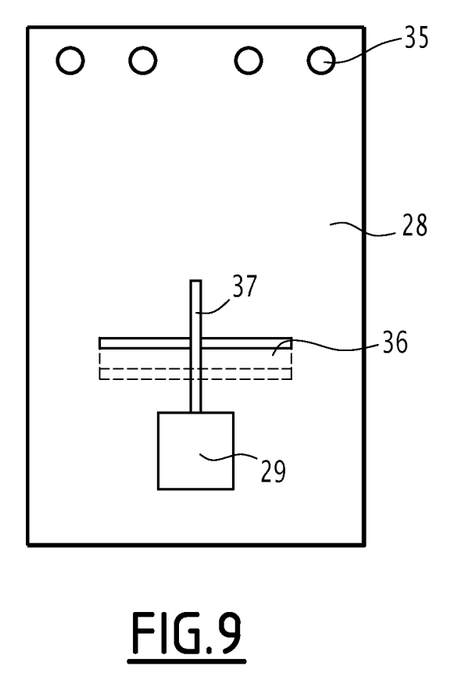
FIG. 9, which shows a front view of the plate of this cutting guide.

This appendage 27 is intended to cooperate with a plate 28 that includes a through orifice 29 emerging on the anterior and posterior faces of the plate 28, and in which the appendage 27 can slide with minimal play. In particular, it is necessary for the angle formed by the plate 28 and the tray 20 to be clearly determined and of permanent value (generally) 90°. It is therefore not advised to give this appendage 27 a circular section that would allow it to rotate easily inside the orifice 29 during the placement and use of the cutting guide.

The position of the plate 28 along the appendage 27 can be fixed, as shown, using through orifices 30, 31, 32, 33 arranged in the appendage 27 and a transverse orifice 34 arranged in the plate 28 and passing through the longitudinal orifice 29. A pin (not shown) or any other functionally similar blocking device can thus be housed in the through orifice 34 of the plate 28 by passing through one of the transverse orifices 30-33 of the appendage 27. It is thus possible to adapt the geometry of the tray 20-plate 28 assembly to those of the tibia of the patient and the tibial implant 1 that will be implanted.

Once this relative position of the plate 28 and the tray 20 is determined and ensured by the blocking device, the cutting guide is fastened to the tibia, for example using nails passing through the longitudinal orifices 35 located in the top part of the plate 28.

Then the cut is made in the bottom anterior end of the tibia, so as to allow the inclined posterior face 8 of the shield 7 of the tibial implant 1 to be placed there. To that end, the plate 28 includes a transverse slit 36 that extends between the anterior face and the posterior face of the plate 28, and which is inclined by an angle equal to the angle α relative to the horizontal. This slit 36 has a width and a thickness that are sufficient to allow a cutting blade to pass and be guided of the conventional type that the surgeon may introduce therein, in order to cut the tibia for reception of the shield 7.

If the tibial implant to be placed includes a single fin 12, the plate 28 also includes a vertical slit 37 located in the transverse median plane of the plate 28. This slit 37 is sized to allow the introduction of a cutting blade to arrange an orifice in the tibia in which the fin 12 will be able to be inserted during the placement of the tibial implant 1. If several fins 12 are provided on the tibial implant 1, it will of course be necessary to provide a similar number of slits 37 in locations corresponding to those of the fins 12.

Before or after the cutting of the tibia as just described, the surgeon cuts the talar bone, which will allow it to receive a talar implant 2 according to the invention. In particular, this cutting tool must be able to arrange a planar top surface on the talar bone, if the top surface 18 of the talar implant 2 is planar, like in the illustrated preferred example. This can be done, for example, using a cutting guide comparable to that described in document WO-A-01/89427.

As stated, these cutting guides, or at least some of them, in particular that intended to prepare the tibia to receive the tibial implant 1 according to the invention and its shield 7 that is specific to the installation of the ankle prosthesis according to the invention, can advantageously be included in a kit including the elements of the ankle prosthesis. This kit can also include cutting tools and means for fastening cutting guides on the corresponding bones of the patient, especially if these cutting tools and fastening means are not of types that are commonly available alone to surgeons. It can also include any other tool to assist the placement of the prosthesis according to the invention, in particular slotted spacers of various thicknesses intended to be used jointly with the tray 20 of the cutting guide of FIGS. 6 to 9 (or any other type of cutting guide based on comparable principles).

An excellent stability of the prosthesis is in particular obtained when the use of a tibial implant 1 with inclined shield according to the invention is combined with an absence of coating/surface treatment on the fins 12, 19 of the implants 1, 2, which minimizes the risk of bone geode formation at the anchors of the implants 1, 2.

The invention claimed is:

1. An ankle prosthesis comprising a tibial implant, a talar implant and an insert with which the tibial implant and the talar implant are articulated,
    wherein each of the tibial implant, the talar implant and the insert has a top face and a bottom face,
    wherein the bottom face of the tibial implant includes a first articulation surface that is articulated with a second articulation surface of the top face of the insert,
    wherein the
    bottom face of the talar implant comprises an anchor for anchoring the talar implant in a talar bone of a patient,
    wherein the top face of the talar implant includes a third articulation surface that is articulated with the second articulation surface of the bottom face of the insert, the third articulation surface of the top face of the talar implant being saddle-shaped and including a longitudinal central groove in which the insert is moveable longitudinally and rotatable transversely,
    wherein the top face of the tibial implant includes a horizontal surface, wherein at least one anchoring fin for anchoring the tibial implant in a tibia of the patient and a shield for covering a bottom anterior portion of the tibia protrude from the horizontal surface,
    wherein the shield is located at an anterior edge of the top face of the tibial implant and includes a posterior surface for being in contact with the tibia and an anterior surface, the posterior surface being inclined relative to the horizontal surface and forming with the horizontal surface a first angle that is oriented forward and is between 15° and 45°, and
    wherein the shield is provided with passages for receiving bone screws, the passages passing through the shield from the anterior surface to the posterior surface in an ascending direction that is inclined relative to the horizontal surface.

2. The ankle prosthesis according to claim 1, wherein the first articulation surface of the bottom face of the tibial implant has a convex shape in a sphere portion and has a curve radius, and wherein the second articulation surface of the top face of the insert has a concave shape in a sphere portion and has a curve radius that is equal to the curve radius of the first articulation surface of the bottom face of the tibial implant.

3. The ankle prosthesis according to claim 1, wherein the first articulation surface of the bottom face of the tibial implant is convex and has a first curve radius in an anterior-posterior plane of the ankle prosthesis, and a second curve radius in a medial-lateral plane of the ankle prosthesis, and wherein the second articulation surface of the top surface of the insert is concave and has curve radii that are the same as said first and second curve radii, the difference between said first and second curve radii being between 1% and 5% of said second curve radius.

4. The ankle prosthesis according to claim 1, wherein the anchor includes at least one transverse fin that is inclined relative to the bottom face of the talar implant by a second angle that is oriented rearward and is between 20° and 70°.

5. The ankle prosthesis according to claim 4, wherein the anchor includes at least two transverse fins that are positioned side by side.

6. The ankle prosthesis according to claim 5, wherein the at least two transverse fins have respective widths the sum of which represents 40% and 80% of a width of the talar implant.

7. The ankle prosthesis according to claim 4, wherein the at least one transverse fin has a width that represents between 40% and 80% of a width of the talar implant.

8. The ankle prosthesis according to claim 1, wherein the at least one anchoring fin has a right-angled triangle shape, the hypotenuse of which rests on the horizontal surface of the top face of the tibial implant and the small side of which is oriented forward.

9. The ankle prosthesis according to claim 8, wherein a length of said hypotenuse represents between 50% and 80% of a total length of the top face of the tibial implant.

10. The ankle prosthesis according to claim 8, wherein an upper corner of the at least one anchoring fin is between 80° and 120°.

11. The ankle prosthesis according to claim 1, wherein the at least one anchoring fin and the anchor have not any surface treatment intended to promote bone growth, whereas other portions of the tibial and talar implants, which are intended to be in contact respectively with the tibia and the talar bone have a surface treatment intended to promote bone growth.

12. The ankle prosthesis according to claim 1, wherein the first angle is equal to 30°.

13. The ankle prosthesis according to claim 1, wherein said direction is inclined relative to the horizontal surface by a second angle that is oriented rearward and is between 60° and 80°.

14. A kit comprising a plurality of ankle prostheses according to claim 1, wherein the ankle prostheses have respective sizes that are different, but have respective curve radii on the bottom faces of their tibial implant which are identical and have respective curve radii on the top faces of their insert which are identical.

15. The kit according to claim 14, further comprising a cutting guide for preparing the tibia to receive the shield.

16. A kit comprising at least one ankle prosthesis according to claim 1 and a cutting guide for preparing the tibia to receive the shield.

\* \* \* \* \*